(12) United States Patent
Akiba

(10) Patent No.: US 7,223,231 B2
(45) Date of Patent: May 29, 2007

(54) ANTI-TWIST CASING FOR ENDOSCOPIC MANIPULATING HEAD ASSEMBLY

(75) Inventor: Haruo Akiba, Saitama (JP)

(73) Assignee: Fujinon Corporation, Saitama (JP)

( * ) Notice: Subject to any disclaimer, the term of this patent is extended or adjusted under 35 U.S.C. 154(b) by 487 days.

(21) Appl. No.: 10/790,007

(22) Filed: Mar. 2, 2004

(65) Prior Publication Data

US 2004/0193011 A1   Sep. 30, 2004

(30) Foreign Application Priority Data

Mar. 26, 2003   (JP)   ............................. 2003-084841

(51) Int. Cl.
*A61B 1/00*   (2006.01)
(52) U.S. Cl. ........................ 600/130; 600/131; 600/146
(58) Field of Classification Search ................ 600/131, 600/101, 146–149
See application file for complete search history.

(56) References Cited

U.S. PATENT DOCUMENTS 4,552,129 A * 11/1985 Utsugi et al. ................ 600/131
6,491,627 B1 * 12/2002 Komi .......................... 600/146
2003/0092965 A1 * 5/2003 Konomura et al. .......... 600/146

* cited by examiner

*Primary Examiner*—John P. Leubecker
(74) *Attorney, Agent, or Firm*—Oblon, Spivak, McClelland, Maier & Neustadt, P.C.

(57) ABSTRACT

A casing of an endoscopic manipulating head assembly is largely constituted by and dividable into a main cover section adapted to support an operating means of an angulation control mechanism and a grip cover section provided between the main cover section and an insertion tube of the endoscope. Both of the main cover section and the grip cover section are formed of a synthetic resin material. A support plate of a rigid metal is provided internally of the manipulating head assembly to support the angulation control mechanism. A plural number of passage-forming tubular structural members are successively connected within the grip cover section for passing internal components to and from the insertion tube of the endoscope. The support plate is connected to one of the tubular structural members which is located at the proximal end of the grip cover section. A first anti-twist lock portion is formed between the support plate and joined end portions of the main and grip cover sections, while a second anti-twist lock portion is formed between the grip cover section and joined end portions of the tubular structural members.

5 Claims, 5 Drawing Sheets

ANTI-TWIST CASING FOR ENDOSCOPIC MANIPULATING HEAD ASSEMBLY

BACKGROUND OF THE INVENTION

1. Field of the Art

This invention relates generally to endoscopes for use in medical fields, and more particularly to a synthetic resin casing of a manipulating head assembly of an endoscope, which is so arranged as to prevent twisting or rotational movements of a grip cover section of the casing.

2. Prior Art

Generally, medical endoscopes are largely constituted by a manipulating head assembly to be gripped by an operator for manipulation of various operation control means, an elongated insertion tube connected to and extended out on the front side of the manipulating head assembly, and a universal cable led out from a rear side of the manipulating head assembly to connect a light guide in the universal cable to a light source. At least an illumination window and an observation window are provided on a rigid tip end section at the fore distal end of the insertion tube. Illumination light is projected forward through the illumination window or windows to illuminate an intracavitary portion of interest during observation or examination through the observation window.

Since the manipulating head assembly is normally gripped and manipulated by one hand of an operator, it is formed of an electrically insulating material on its exterior surfaces and, for reduction of weight, housing in a casing of synthetic resin material. An angulation control mechanism is mounted in the casing of the manipulating head assembly for angularly bending an angle section which is provided at the fore end of the endoscopic insertion tube. In addition, a light guide or guides, signal cable, biopsy channel tube, air/water feed tube, angulation control wires are threaded through the manipulating head assembly of the endoscope. In order to support these internal components, a support plate and a tubular passage member, both of metal, are provided within the casing of the manipulating head assembly. The support plate is provided for supporting the angulation control mechanism and at the same time for guiding certain threaded member. The tubular passage member serves to enhance the shape retainability and strength of the manipulating head assembly. The support plate and the passage member are connected with each other. Normally, the passage member has a tubular body which is composed of a plural number of parts which are joined with each other by the use of screws or other fixation means.

Of the above-mentioned support plate and the tubular passage member which are accommodated within the casing of the manipulating head assembly of the endoscope, the support plate is required to have relatively high structural strength for supporting the angulation control mechanism. Therefore, the casing of the manipulating head assembly is arranged as a cover having an increased wall thickness at least in an angulation mechanism mount portion. On the other hand, the casing of the manipulating head assembly is not required to have high strength in particular from a grip portion to a fore end portion which is connected to the insertion tube. Therefore, the grip portion of the casing is usually reduced in wall thickness to cut the total weight of the casing. Further, a divisional cover section with an entrance to the biopsy channel is provided between a grip cover section and a main cover section. A manipulating head assembly with these casing arrangements is well known in the art, for example, from Japanese Patent Publication H5-3287.

In this connection, the manipulating head assembly is gripped by an operator at the grip cover section which is formed of thin wall synthetic resin material, so that twisting forces are applied to the grip cover section of the casing during use. Therefore, the casing of the manipulating head assembly is usually provided with an anti-twist mechanism for preventing deformations of the grip cover section by rotational twisting forces. In the case of the prior art mentioned above, an anti-twist mechanism for the grip cover section is constituted by a metallic reinforcing member provided internally of the grip cover section, and a link member provided for connection to a reinforcing tube provided internally of the divisional cover section and having a flat surface on a lateral side face to face with and in small gap relation with a flat surface on a lateral inner surface of the grip cover section of the casing. When a twisting force is applied to the grip cover section, the two flat surfaces are brought into abutting engagement with each other to prevent rotational movements of the grip cover section.

The grip cover anti-twist mechanism by the above-mentioned prior art however still has a number of problems. Namely, restrictions are imposed on the inner and outer surfaces of the grip cover section and the link member. Particularly in a case where the grip section of the casing is formed approximately in a circular shape in section, a difficult machining operation is required to provide a flat surface on the inner side of the grip cover section, and the weight of the manipulating head assembly is inevitably increased for this reason. Besides, difficulties are encountered in directly connecting the reinforcing member, which is provided across the main cover section and the grip cover section of the casing, to the reinforcing tube which is provided internally of the divisional cover section. In addition to an increased number of parts, the use of the link member results in a restriction on the available internal space of the manipulating head assembly.

SUMMARY OF THE INVENTION

In view of the foregoing situations, it is an object of the present invention to provide a casing for an endoscopic manipulating head assembly, which is provided with anti-twist lock portions to prevent twisting or rotational movements of a grip cover section of the casing.

It is another object of the present invention to provide a casing of the sort mentioned above, which is largely constituted by a main cover section and a grip cover section both formed of a synthetic resin material to provide a lightweight casing and which is arranged to enhance the strength of the grip cover section despite a reduction in wall thickness.

In accordance with the present invention, for achieving the above-stated objectives, there is provided a casing for endoscopic manipulating head assembly, the casing being formed of a synthetic resin material and largely constituted by a main cover section and a grip cover section, the main cover section being adapted to support thereon an operating member of an angulation control mechanism, and the grip cover section being projected forward from the main cover section to provide a grip portion between the main cover section and an insertion tube of the endoscope, characterized in that the casing comprises: a rigid support plate provided mostly within the main section and partly in the grip cover section to support the angulation control mechanism; a plural number of passage-forming tubular structural members successively connected one after another within the grip cover section for passing internal components to or from the insertion tube of the endoscope, a tubular member at the proximal end of the grip cover section being connected to the rigid support plate; a first anti-twist lock portion for blocking rotational movements of the grip cover section relative to the main cover section, formed by the support plate between the main cover section and a proximal end of the grip cover section connected to the main cover section; and a second anti-twist lock portion formed between a joint portion of the tubular members and the grip cover section of the casing.

According to the present invention, a manipulating head assembly of an endoscope is housed in a casing which is largely constituted by two parts, i.e., a main cover section and a grip cover section. An anti-twist lock portion is formed by the support plate on the side of the proximal end of the grip cover section, and another anti-twist lock portion is formed by engagement with passage-forming tubular structural members on the side of the fore end of the grip cover section. The first anti-twist lock portion is formed by engaging opposite side edges of the support plate with axial grooves which are provided on the inner side of the casing. The second anti-twist lock portion is formed by an axial protuberance which is formed on an inner surface of the grip cover section and adapted to be tightly fitted in an axial groove which is provided on the part of a passage-forming tubular structural member. In a preferred form of the invention, a tubular passage is formed within the grip cover section not by a single tubular structural member but three tubular structural members which are successively connected end to end in the axial direction, i.e., a first tubular member which is connected to the support plate, a third tubular member which is connected to the insertion tube of the endoscope, and a second tubular member which is connected between the first and third tubular members and in which a branching pipe member is located to connect a biopsy channel tube with a biopsy channel entrance pipe and a suction tube. The second tubular member is provided with a large diameter portion at its proximal end for fitting engagement with the first tubular member. An axial locking groove is provided on the large diameter portion for tight fitting engagement with an axial protuberance or a rib portion which is provided on the side of the grip cover section. Thus, anti-twist lock portions can be provided on the casing without adding special parts for this purpose.

The above and other objects, features and advantages of the present invention will become apparent from the following particular description of the invention, taken in conjunction with the accompanying drawings which show by way of example some preferred embodiments of the invention.

DESCRIPTION OF PREFERRED EMBODIMENTS

Figure 1:
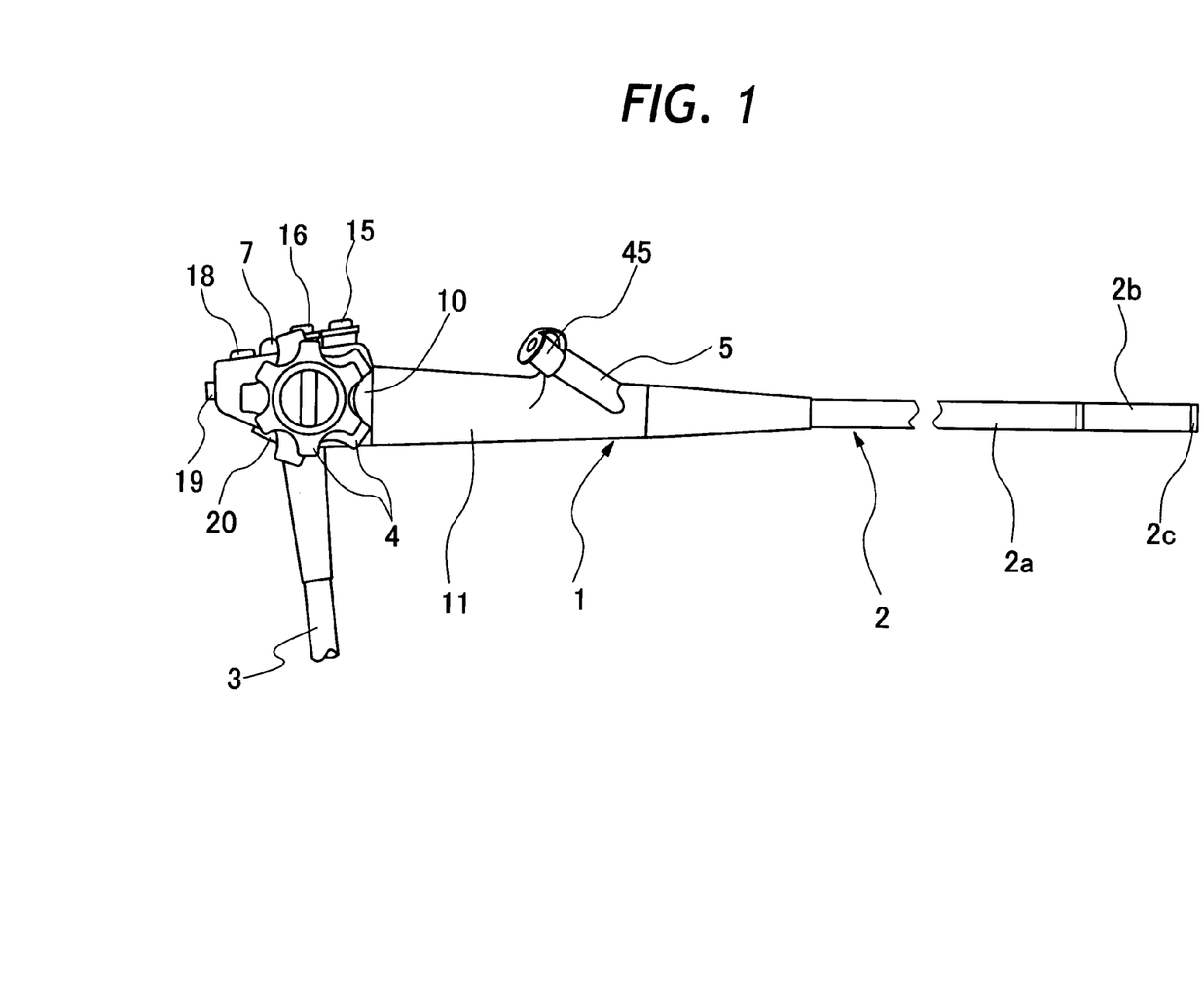
FIG. 1 is a schematic sectional view of a manipulating head assembly of an endoscope, taken through a main cover section of its casing.

Hereafter, the present invention is described more particularly by way of its preferred embodiments. Referring first to FIG. 1, there is schematically shown the general layout of an endoscope. In that figure, indicated at 1 is a manipulating head assembly of the endoscope, at 2 an insertion tube, and at 3 a flexible light guide cable. From a proximal end which is connected to the manipulating head assembly 1, a major part of the insertion tube 2 consists of an elongated flexible body portion 2a which can be bent in arbitrary directions at the time of insertion into a body cavity. Successively connected to the fore end of the flexible body portion 2a are an angle section 2b and a rigid tip end section 2c. As well known in the art, illumination and observation windows are provided on the rigid tip end section 2c which can be turned into an arbitrary direction by angulation of the angle section 2c.

The angulation of the angle section 2b is controlled from the side of the manipulating head assembly 1. For this purpose, an angulation knob 4 is provided on the manipulating head assembly 1 as an operating member of the angulation control mechanism. Further, in order to permit insertion of a biopsy or surgical instrument such as forceps and high frequency tool, an exit way (not shown) of a biopsy channel is opened in the vicinity of the endoscopic observation window, while an entrance way 5 to the biopsy channel is provided on the manipulating head assembly 1. Connected between the entrance way 5 on the manipulating head assembly 1 and the exit opening on the rigid tip end section 2c is a biopsy channel 30 including a flexible biopsy channel tube which is flexible in bending direction as described in greater detail hereinlater.

For manipulation of the endoscope, an operator grips the manipulating head assembly 1 by holding with one hand a grip cover section between the biopsy channel entrance way 5 and the angulation knob 4. The angulation knob 4 is turned by a finger of the operator's hand which holds the manipulating head assembly 1, normally by a thumb of the operator's hand. As the angulation knob 4 is turned by an operator, angulation control wires are pulled in a forward or backward direction to angularly bend the angle section 2b into a desired direction. Further, the operator uses the other hand at the time of inserting a treating instrument into the biopsy channel entrance way 5 on the manipulating head assembly 1.

In this connection, from the standpoints of electrical insulation and lightness in weight, the cover casing of the manipulating head assembly 1 is normally composed of synthetic resin moldings. A cover section to be assembled with the angulation knob 4 is increased in wall thickness, that is to say, increased in strength because greater loads are imposed there. On the other hand, a cover section which is located forward of the angulation knob 4 can be reduced in wall thickness because no greater force than operator's gripping force is imposed on that section. Various component parts are built into the casing of the manipulating head assembly, and the casing should allow access to such internal component parts for maintenance and service. Therefore, the casing of the manipulating head assembly 1 is arranged to be split into two parts, more particularly, into a main cover section 10 on the proximal side, including a mount portion for the angulation knob 4, and a grip cover section 11 extending from the main cover section 1 to a fore distal end which is coupled with the insertion tube 1 of the endoscope. As compared with the grip cover section 11, the main cover section 10 is greater in wall thickness. From the standpoint of reducing the weight of the manipulating head assembly 1, it is desirable to make the length of the thick-walled main cover section 10 as short as possible and to use the thin-walled grip cover section 11 in those portions where large external forces would not be applied.

Figure 2:
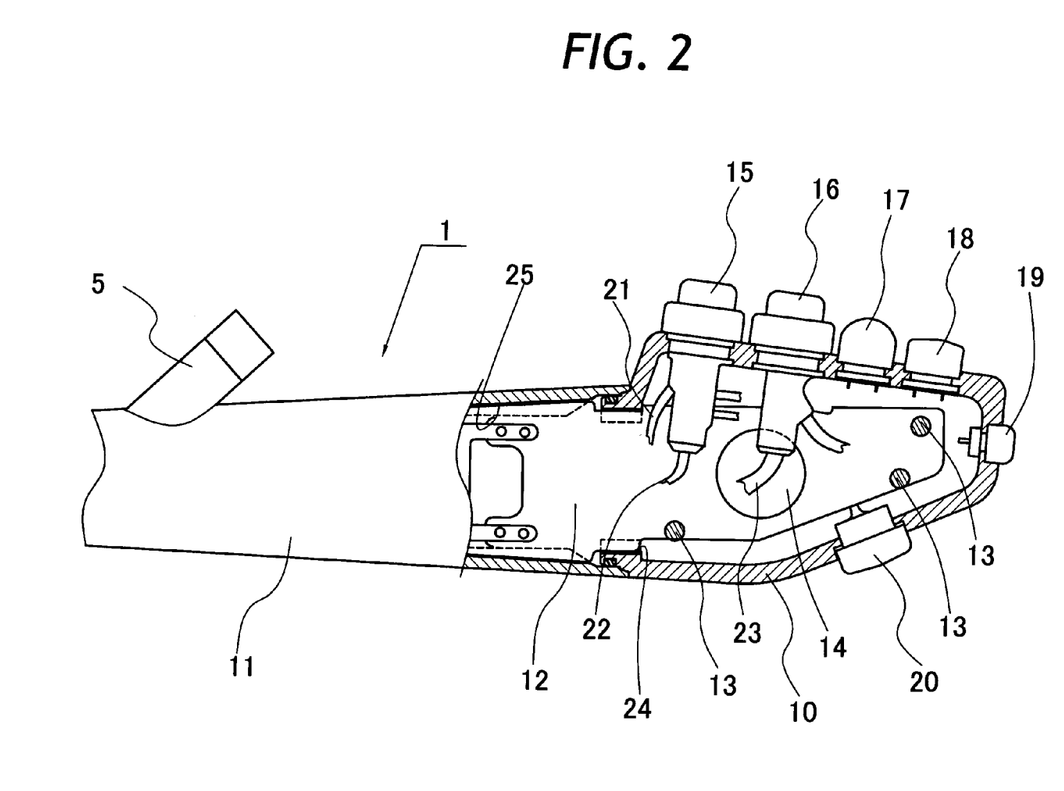
FIG. 2 is a schematic sectional view of the manipulating head assembly of the endoscope, taken through a grip cover section of the casing.
Figure 3:
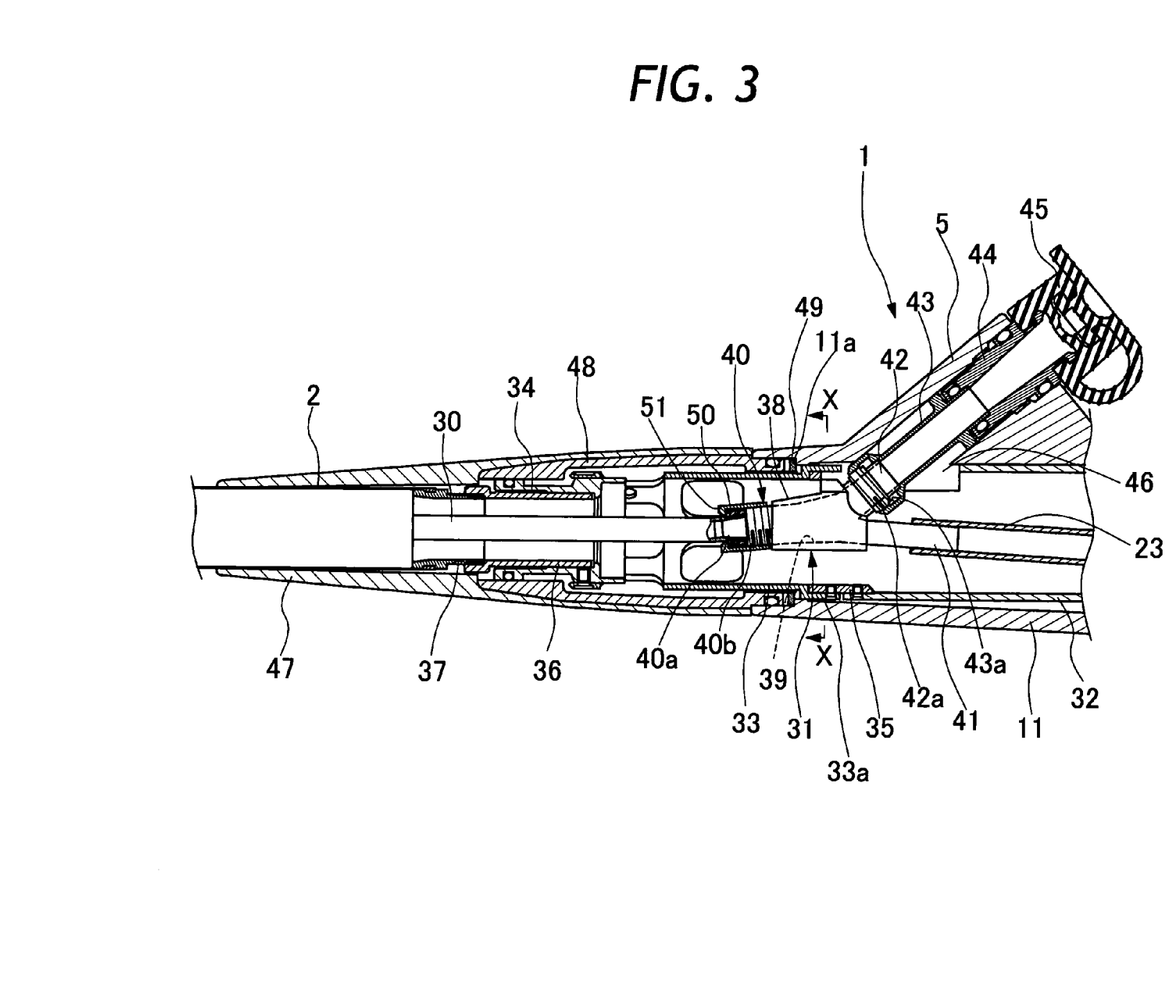
FIG. 3 is a schematic sectional view of the manipulating head assembly of the endoscope, taken through a grip cover section of the casing.

Turning now to FIGS. 2 and 3, there are shown internal constructions of the main cover section 10 and the grip cover section, respectively.

As seen in FIG. 2, a rigid support plate 12 is provided internally of the main cover section 10. This rigid support plate 12 is formed of a light metallic material such as an aluminum alloy or the like, and securely fixed to a plural number of posts 13 which are erected within the main cover section 10 by means of screws or other suitable fixation means. Mounted on the support plate 12 is a pulley 14 of an angulation control means, which is coupled with and turned by the angulation knob 4. Further, provided on the main cover section 10 are an air/water feed valve 15 and a suction valve 15 along with various switches 17 to 20 which are operated by operator's fingers from the grip cover section 11. An air feed tube 21 and a water feed tube 22 from the air/water feed valve 15 are extended and passed into the insertion tube 2. A suction tube 23 is connected to the suction valve 16. Furthermore, axial grooves 24 and 25 are provided on a fore end portion of the main cover section 10 and on a proximal end portion of the grip cover section 11, respectively. The support plate 12 is fixedly fitted in these grooves 24 and 25 in such a way as to block relative rotational movements of the main cover section 10 and the grip cover section 11.

Accommodated in the grip cover section 11 are various component parts to be threaded through the insertion tube 2, including a light guide, signal cable, air feed tube 21, water feed tube 22 and angulation control wires. As shown in FIG. 3, a proximal end portion of the biopsy channel tube 30, which is connected to the biopsy channel entrance way 5, is extended into the grip cover section 11. Since the biopsy channel tube 30 is also utilized as part of a suction tube, a fore end portion of the suction tube 23 from the suction valve 16 is connected to the biopsy channel tube 30. Therefore, the proximal end of the biopsy channel tube 30 needs to be divided into two branch passages which are in communication with the biopsy channel entrance way 5 and the suction tube 23, respectively. For this purpose, a bifurcated branching member 31 is located in the vicinity of the biopsy channel entrance way 5.

The bifurcated branching member 31 is located internally of the grip cover section 11, and internally of passage-forming tubular structural members which are provided within the main and grip cover sections for threading the above-mentioned component parts. The just-mentioned passage-forming structural members are formed of a metal sheet which is thin but has sufficient strength from the standpoint of protection of internal component parts and shape retainability. In this regard, in order to reduce the weight of the casing as much as possible, it is preferable to use aluminum or an aluminum alloy such as Duralumin or other light metals, and to connect a plural number of tubular structural members depending upon respective functions. Namely, in the case of the particular embodiment shown, the passage-forming structural members are constituted by a first tubular member 32, a second tubular member 33 and a third tubular member 34, from the side of the main cover section 10. A base end portion of the first tubular member 32 is connected to the support plate 12 by means of screws or the like, while its fore end is connected to the second tubular member 33 through a reinforcing ring 35. Further, a fore end portion of the second tubular member 33 is placed in the third tubular member 34 and connected to the latter by means of screws or the like. Furthermore, a connector ring 36 is threaded into the third tubular member 34, and in turn the connector ring 36 is threaded into a fixed ring 37 which constitutes a base end of the insertion tube 2. The reinforcing ring 35 is constituted by a narrow ring to connect the first and second tubular members 32 and 33 with each other and made of stainless steel to provide a connection of enhanced strength. At a base end, the second tubular member 33 is provided with a larger diameter portion 33a which cover fore end portions of the reinforcing ring 35.

The branching pipe member 31 which is located internally of the passage-forming structural members is provided with a bifurcated passage 38 within a metallic casing body 38, with a first connection terminal 40 to be connected with the biopsy channel tube 30, a second connection terminal 41 to be connected with the suction tube 23 and a third connection terminal 42 to be connected with a biopsy channel entrance way pipe 43 which is fitted in the biopsy channel entrance way 5. More specifically, the biopsy channel entrance way pipe 43 is fitted in a mouth piece member 44 which is threaded into the biopsy channel entrance way 5. The mouth piece member 44 is projected from a proximal end of the biopsy channel entrance way 5, and a plug member 45 is fitted on the projected outer end of the mouth piece member 44. Accordingly, the third connection terminal 42 of the branching pipe member 31 has to be projected toward the biopsy channel entrance way pipe 43 through the passage-forming structural members within the grip cover section 11. The third connection terminal 42 is projected at an axial position where the first tubular member 32 is connected with the reinforcing ring 35. Therefore, a notched portion 46 is provided at the connection of the reinforcing ring 35 and the first tubular member 32 to receive the third connection terminal 42 to be connected to the biopsy channel entrance way pipe 43.

The grip cover section 11 is extended to such an axial position as to enshroud base end portions of the second tubular member 33. A rubber cover 47 is fitted on a fore end portion of the grip cover section 11 in such a way as to encase a proximal end portion of the insertion tube 2 over a predetermined length. For the purpose of retaining the shape of the rubber cover 47, the rubber cover 47 is integrally provided with a shape retaining tube 48 on the inner side thereof. This shape retaining tube 48 is fixedly threaded into the second tubular member 33. Further, an external screw is provided on the outer periphery of the second tubular member 33 for threaded engagement with a screw ring 49. This screw ring 49 is pressed against a stopper wall 11a which is provided on a fore end portion of the grip cover section 11. As a result, the grip cover 11 is constantly biased in the direction of the 11 main cover 10 and held in pressed engagement with the latter.

In the case of the particular embodiment shown, a major part of the branching pipe member 31 is located internally of the second tubular member 33, and the second connection terminal 41 is extended in the direction of the first tubular member 31. Further, the third connection terminal 42 is extended obliquely upward direction through the notched opening 46 and connected with the biopsy channel entrance way pipe 43. Therefore, after removing the plug member 45, a treating instrument can be inserted into the biopsy channel entrance 30 through the mouth piece 44, entrance way pipe 43 and the passage 39 of the branching pipe member 31. Further, when the entrance way 5 is hermetically closed by the plug member 45, an aspirator can be connected to the suction tube 2, for example, for aspiration of body fluids to the suction tube 23 from the biopsy channel tube 30 via passage 39 of the branching pipe member 31.

By the way, the grip cover section 11 has a prevailing length on the casing of the manipulating head assembly 1. Therefore, when it is gripped by an operator to manipulate various operating means on the manipulating head assembly 1, the grip cover section 11 can be twisted by application of a twisting force which occurs as a result of manipulation of the endoscope. More specifically, the flexible light guide cable 3 is led out from the main cover section 11 which is connected to the proximal end of the grip cover section 11. On the other hand, the insertion tube 2 of the endoscope, which is connected with the passage-forming structural members, is extended out from the fore end of the grip cover section 11. Therefore, if the grip cover section 11 is twisted, it tends to rotate relative to the main cover section 10 or relative to the insertion tube 2. Since the grip cover section 11 is reduced in wall thickness, it can be deformed or damaged by application of twisting forces.

In order to preclude such troubles, the grip cover section 11 is provided with anti-twist lock portions at its opposite axial ends. As shown in FIG. 2, a first anti-twist lock portion at the proximal end of the grip cover section 11 is constituted by axial grooves 25 which are engaged with opposite side edge portions of the support plate 12. The support plate 12 is fixed to the thick-walled main cover section 10 and engaged with the axial grooves 24 which are provided at the fore end of the main cover section 10 which is coupled with the grip cover section 10. The above-mentioned grooves 25 on the side of the grip cover section 11 are formed in the axial direction continuously from the grooves 24 on the side of the main cover section 10. Therefore, even if a twisting force is exerted on a proximal end portion of the grip cover section 11, the support plates 12 which is a rigid and strong member acts to block rotational movements of the grip cover section 11 relative to the main cover section 10.

Normally, the grip cover section 11 of the manipulating head assembly 1 is gripped by an operator at a position on the proximal side of the biopsy channel entrance way 5. In the internal space of the grip cover section 11, the branching pipe member 31 which is in communication with the biopsy channel entrance way 5 is located within the second tubular member 33, more particularly, on the side of the reinforcing ring 35 which connects the second tubular member 33 with the first tubular member 32.

Figure 4:
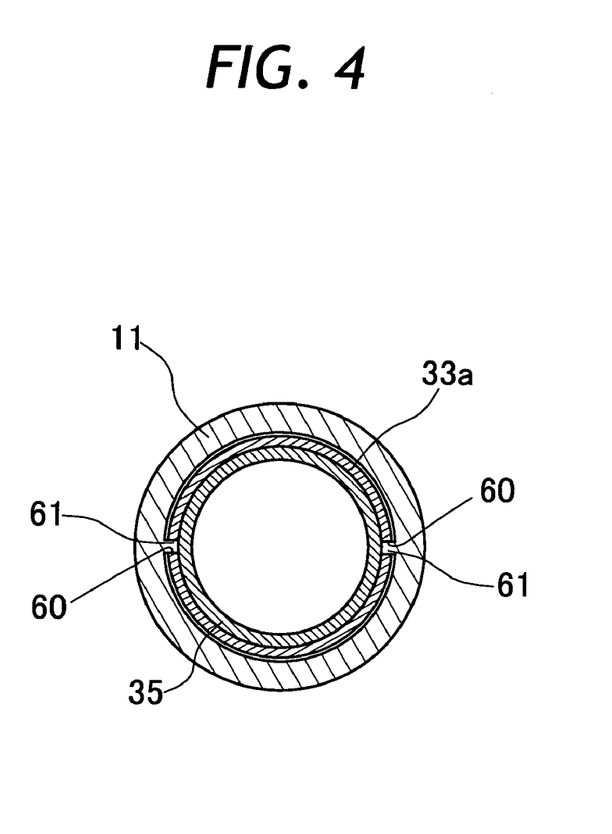
FIG. 4 is a sectional view taken in the direction of arrows X—X in FIG. 3.
Figure 5:
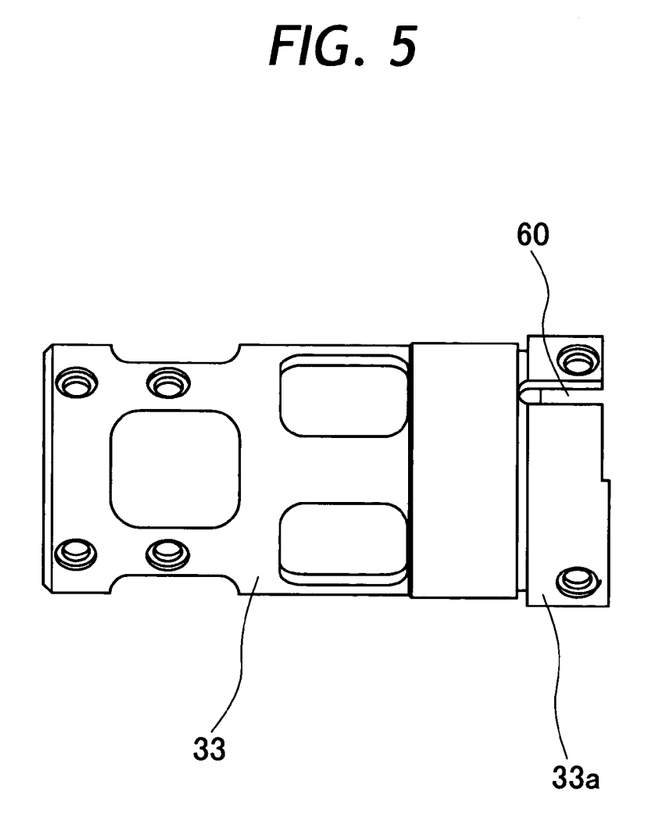
FIG. 5 is a schematic front view of a second tubular member.

As shown in FIGS. 4 and 5, a second anti-twist lock portion is provided between the second tubular member 33 and the grip cover section 11. More specifically, the proximal end of the second tubular member 33 is fitted on the reinforcing ring 35 to presents itself as a large diameter portion 33a, and a plural number of slot-like axial grooves 60 (two axial grooves in the particular embodiment shown) are formed on the large diameter portion 33a. On the other hand, for tight fitting engagement with these grooves 60 on the second tubular member 33, a corresponding number of inwardly projecting axial protuberances or ribs 61 are formed at corresponding angular positions on the inner surface of a fore end portion of the grip cover section 11 forward of the biopsy channel entrance way 5.

With the anti-twist lock portions as described above, at the front end of the grip cover section 11, the axial projection 61 is held in engagement with the axial groove 60 to prevent twisting rotational movements of the grip cover section 11. In this instance, the screw ring 49 in threaded engagement with the second tubular member 33, a second one of the three first to third tubular members 32 to 34 which are successively connected with each other as passage-forming structural members, is pressed against the stopper wall 11a of the grip cover section 11. It follows that the grip cover section 11 is pushed against the main cover section 10 by the pressure which is applied by the screw ring 49. Of the first to third tubular members 32 to 34 serving as structural members of an elongated passage, the second tubular member 33 in the middle is retained in position because it is restricted of spontaneous movements by the action of the screw ring 39 and the engagement of the projection 61 with the groove 60. Besides, the shape retaining tube 48 is threaded with the second tubular member 33 which is blocked against deviating movements relative to the grip cover section 11. As a consequence, connected portions of the grip cover section 11 and the rubber cover member 47 are maintained in a stable state.

What is claimed is:

1. In a casing for manipulating a head assembly of an endoscope, said casing being formed of a synthetic resin material and largely constituted by a main cover section and a grip cover section, said main cover section being adapted to support thereon an operating member of an angulation control mechanism, and said grip cover section being projected forward from said main cover section to provide a grip portion between said main cover section and an insertion tube of said endoscope:

a rigid support plate provided mostly within said main cover section and partly in said grip cover section to support said angulation control mechanism;

a passage forming structure for passing through internal components to or from said insertion tube of said endoscope comprising a plural number of tubular members successively connected one after another within said grip cover section, a base end tubular member of said passage forming structure being connected to said rigid support plate and a fore end tubular member thereof being connected to said insertion tube;

a first anti-twist lock portion for blocking rotational movements of said grip cover section relative to said main cover section; and a second anti-twist lock portion formed between a joint portion of said passage forming structure and said grip cover section of said casing;

wherein said first anti-twist lock portion being formed by placing opposite edge portions of said support plate in a pair of axial grooves provided on inner surfaces of said main and grip cover sections of said casing.

2. A casing for manipulating the head assembly of the endoscope as defined in claim 1, wherein said base end tubular member being connected to at least one intermediate tubular member through a reinforcing ring, and said fore end tubular member being inserted into a fore end of said intermediate tubular member.

3. A casing for manipulating the head assembly of the endoscope as defined in claim 2, wherein said base end tubular member, said at least one intermediate tubular member and said fore end tubular member are formed of a light metal, and said reinforcing ring is of stainless steel.

4. A casing for manipulating the head assembly of the endoscope as defined in claim 3, wherein said base end tubular member, said at least one intermediate tubular member and said fore end tubular member are formed of aluminum or an aluminum alloy.

5. A casing for manipulating the head assembly of the endoscope as defined in claim 1, wherein said second anti-twist lock portion is formed by an axial groove provided on a large diameter portion at a fitting joint portion of said base end tubular member, and an axial projection or rib provided on an inner surface of said grip cover section for tight fitting engagement with said axial groove.

* * * * *